United States Patent [19]

Åkerström

[11] 4,407,303

[45] Oct. 4, 1983

[54] ENDOCARDIAL ELECTRODE ARRANGEMENT

[75] Inventor: Bengt Åkerström, Täby, Sweden

[73] Assignee: Siemens Aktiengesellschaft, Berlin & Munich, Fed. Rep. of Germany

[21] Appl. No.: 252,428

[22] Filed: Apr. 9, 1981

[30] Foreign Application Priority Data

Apr. 21, 1980 [DE] Fed. Rep. of Germany ....... 3015260

[51] Int. Cl.³ .............................................. A61N 1/04
[52] U.S. Cl. .................................... 128/785; 128/786; 128/419 P
[58] Field of Search .............................. 128/784–786, 128/419 P, 642

[56] References Cited

U.S. PATENT DOCUMENTS

| | | |
|---|---|---|
| 3,902,501 | 9/1975 | Citron et al. |
| 4,026,303 | 5/1977 | Babotai ................................ 128/785 |
| 4,258,724 | 3/1981 | Balat et al. ........................... 128/785 |
| 4,301,815 | 11/1981 | Doring ................................ 128/785 |

FOREIGN PATENT DOCUMENTS 9732 4/1980 European Pat. Off. ............ 128/785

*Primary Examiner*—Lee S. Cohen
*Attorney, Agent, or Firm*—Hill, Van Santen, Steadman & Simpson

[57] ABSTRACT

In an exemplary embodiment useful for the intracardiac stimulation of the heart, an elongated electric conductor is provided with an electric insulation covering, and has an electrode head which is electrically conductively connected with the distal end of the conductor, serving the purpose of supplying the stimulation pulses to the heart. The conductor or the electrode head is to be emplaced on the heart wall. It is the object of the disclosure to produce an endocardial electrode arrangement of the type initially cited which is readily embedded as a result of tissue growth and which nevertheless has a comparatively small volume. In accordance with the disclosure, this object is achieved in that, for the purpose of placement of the conductor, or of the electrode head, a loop or a plurality of loops consisting of soft, thin material is provided which is mounted on the electrode head or on the electric insulation of the elongated electric conductor in proximity of the electrode head.

14 Claims, 8 Drawing Figures

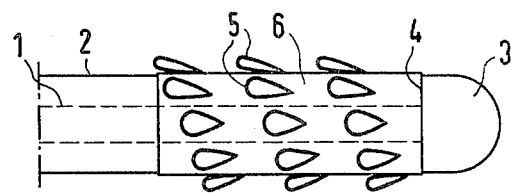
FIG 1
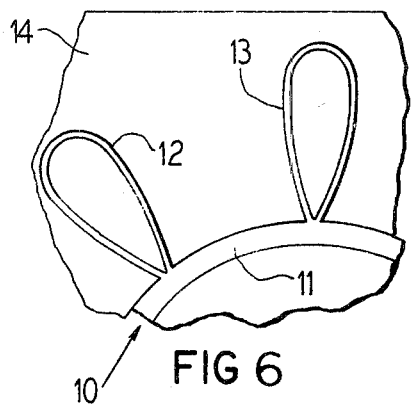
FIG 6
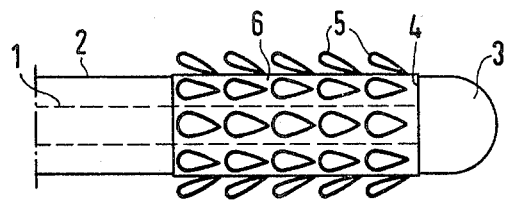
FIG 2
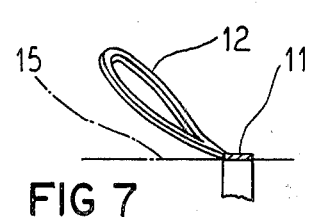
FIG 7
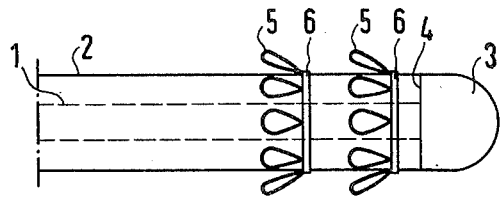
FIG 3
FIG 4
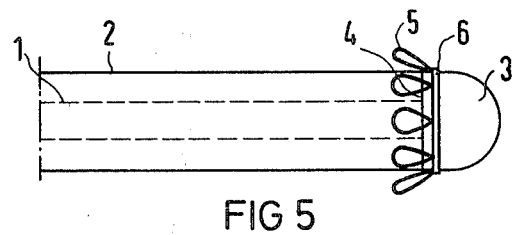
FIG 5
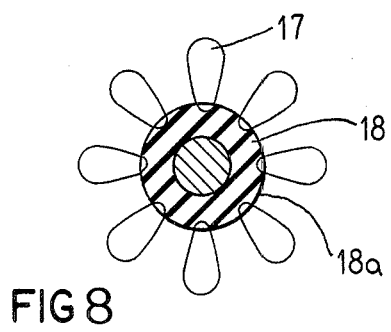
FIG 8

ENDOCARDIAL ELECTRODE ARRANGEMENT

BACKGROUND OF THE INVENTION

The invention relates to an endocardial electrode arrangement for the intracardiac stimulation of the heart, comprising an elongated electric conductor which is provided with electrical insulation, and an electrode head which is electrically conductively connected to the distal end of the conductor, serving the purpose of applying stimulation pulses to the heart, and means for the placement of the conductor, or the electrode head, respectively, on the heart wall.

From the U.S. Pat. No. 3,902,501, an endocardial electrode of this type is known. In the case of this electrode, relatively stiff tines consisting of silicone rubber directly behind the electrode head serve as placement means which, after application, engage in the heart tissue and thus retain the electrode in position. The insertion of such an electrode in a vein, particularly one having a small diameter, such as e.g., in the case of children, however, presents appreciable difficulties on account of the relatively voluminous electrode head. In the case of atrium-controlled heart pacemakers, as a rule, even two electrodes are inserted. Even in the case of veins having a diameter of normal size, two electrode heads can barely be placed. The tines also hardly permit subsequent corrections of the position; their growth onto the heart wall is rendered difficult, since the connective tissue is offered a small space for growth around said tines.

SUMMARY OF THE INVENTION

The object underlying the invention resides in creating an endocardial electrode arrangement of the type initially cited which achieves good emplacement within the heart and which nevertheless has a comparatively small volume.

In accordance with the invention this object is achieved in that, for the placement of the conductor, or of the electrode head, respectively, a loop or plurality of loops of soft thin material is provided which is mounted on the electrode head or on the electric insulation of the elongated electric conductor in proximity of the electrode head.

Loops of a soft, thin material, upon insertion of the electrode in a vein also having a very small diameter, lie closely against the electrode. Thus, the insertion hardly meets with resistance. In addition, the flexibility of the loop material permits local corrections of a random nature without the trabecula being damaged. Moreover, connective tissue rapidly and readily grows into the loops, so that the electrode becomes well fixed on the heart wall. An additional advantage of the loops lies in that, upon passage of the electrode through a vein, the loops become filled with blood coagulate. The blood coagulate acts as an adhesive, so that the loops become securely adhesively attached to the heart wall, which leads to a particularly rapid growing into position of the electrode.

An additional advantage can be seen in that the inventive electrode, on account of its small diameter, can be employed in the case of a subclava punction. In the case of a subclava punction, without a surgical incision, a catheter of a small diameter is punctured through the subclava. The electrode is then inserted through the catheter into the vessel to the heart.

An advantageous further development of the invention is that the loops consist of a reabsorbable material. What is achieved thereby is that the implanted electrode, at a later time, can be very readily removed, since the loops dissolve in time.

Further details shall be apparent from the subclaims.

The invention shall be explained in greater detail on the basis of several exemplary embodiments illustrated in the figures of the accompanying drawing sheet; and other objects, features and advantages will be apparent from this detailed disclosure and from the appended claims.

BRIEF DESCRIPTION OF THE DRAWINGS

FIG. 1 illustrates the distal end of an inventive endocardial electrode arrangement;

FIGS. 2 and 3 illustrate variants of the endocardial electrode arrangement according to FIG. 1;

FIG. 4 illustrates the endocardial electrode arrangement according to FIG. 3 in a frontal view;

FIG. 5 illustrates a variant of the endocardial electrode arrangement according to FIG. 3;

FIG. 6 is a somewhat diagrammatic partial plan view illustrating a step in the forming of an electrode arrangement in accordance with FIG. 3;

FIG. 7 is a partial longitudinal sectional view and illustrating exemplary detailed construction for the embodiment of FIG. 3; and FIG. 8 is a somewhat diagrammatic cross sectional view illustrating a further embodiment of the present invention.

DETAILED DESCRIPTION

In FIG. 1, 1 designates the electric conductor of an electrode. It is provided with an electric insulation sheath or covering 2. At the distal end the electrode head 3 is disposed which is essentially cylindrically designed and rounded at its free end. The head can also exhibit other shapes; for example, pure non-rounded cylinder shape, or the like. At its rear end 4 the electrode head 3 is electrically and mechanically connected to the electric conductor 1. After application of the electrode head 3 on the heart wall, stimulation pulses can be supplied to the heart via conductor 1 and electrode 3.

In order that the electrode be securely retained in its position in the heart, loops 5 are provided in proximity to the electrode head 3 into which loops heart tissue can grow. In FIG. 1, the loops 5 are mounted on a sleeve 6 which is slipped over the insulation 2. The loops 5 are here attached along a helical-shaped line.

In the electrode of FIG. 2, the loops 5 are mounted on the sleeve 6, distributed on the circumference along parallel lines which run in the longitudinal direction of the elongated conductor 1.

In the electrode of FIG. 3, several collars 6, which are provided with loops 5, are slipped on the insulation 2 of the conductor 1, which collars are spaced apart from one another.

The electrode of FIG. 4 illustrates the collar 6 with loops in a frontal perspective. This type of design renders possible punching out as a complete punched (or stamped) part.

The electrode of FIG. 5 illustrates an arrangement of a collar 6 with loops 5 on the electrode head 3.

The loops can be fabricated from a soft, thin, body-fluid-resistant material, such as e.g., polyester or polypropylene. For the purpose of fabrication it is likewise possible to also employ a reabsorbable material, such as e.g., cat gut, which, in the case of an implanted electrode, dissolves in time so that an electrode exchange, as required, is possible without complications. Instead of on sleeves or collars, the loops can also be directly attached to the electric insulation 2. They project above the surface of the electrodes by approximately one to five millimeters (1 to 5 mm). Due to the fact that the loops 5 consist of a very soft and thin material, independently of number and size, they rest close against the electrode during insertion of the electrode in a vein. With the smallest diameter of the electrode, there is hardly any resistance during insertion. Upon insertion of the electrode, blood coagulate also is collected in the loops, which coagulate, as an adhesive, facilitates the secure growing in place of the electrode on the heart wall.

It will be apparent that many modifications and variations may be effected without departing from the scope of the novel concepts and teachings of the present invention.

Supplementary Discussion

FIG. 6 illustrates the fabrication of a loop assembly 10 including a ring 11 and loops such as 12 and 13 from a sheet 14 of a soft, thin, body-fluid-resistant material such as for example polyester or polypropylene. The loop assembly 10 can be punched out as a complete punched part from the sheet 14. Further as illustrated in FIG. 7, and in FIG. 3, each of the loops such as 12 can be formed relative to the ring or collar 11 so that when the collar 11 encircles the electric insulation covering 2 as shown in FIG. 3 or the electrode head 3 as shown in FIG. 5, the loops project above the surface of the electrode which is indicated at 15 in FIG. 7 by a radial distance of approximately one to five millimeters. Upon insertion of the electrode into a vein, however, the loops such as 12 are pressed against the external surface 15, FIG. 7, in a resilient manner, so that the loops can return to the configuration as shown in FIGS. 1–5 and 7, upon emplacement of the electrode on the heart wall.

For the material 14, FIG. 6, it is also possible to employ a reabsorbable material such as for example cat gut which in the case of an implanted electrode, dissolves in time so that an electrode exchange, as required, is possible without complications.

As indicated in FIG. 8, instead of forming the loops such as indicated at 12 and 13, FIG. 6, integrally with collars as shown in FIGS. 3 and 5, loops as indicated at 17 in FIG. 8 can also be directly attached to the electrical insulation 18 forming the insulating covering such as indicated at 2 in FIGS. 1, 2, 3 and 5. Again, the loops 17 are so secured and have a sufficient stiffness so as to normally project above the surface 18a by a radial distance of approximately one to five millimeters. Again, the loops 17 are formed of a soft, thin, resilient material such as polyester or polypropylene so that the loops will rest against the external surface 18 of the electrode during insertion of the electrode in a vein.

The surface 15, FIG. 7, and the surface 18, FIG. 8, defines a cylindrical electrode configuration in proximity to the electrode head 3, FIG. 7 illustrating exemplary detailed construction for the embodiment of FIG. 3. As previously stated, the ring or collar 11 can encircle the electric insulation covering 2 as shown in FIG. 3 or the electrode head 3 as shown in FIG. 5. As indicated in FIG. 7, each loop 12 may comprise a base portion such as indicated at 11 with two elongated strip portions formed from the sheet 14, FIG. 6, extending from the base portion 11 in spaced relationship and in a direction away from the electrode head 3. Each loop also comprises an arcuate connecting strip portion of the material 14, FIG. 6, which connects the two elongated strip portions at the region thereof remote from the base portion 11 so as to form a loop configuration with an opening therethrough.

I claim as my invention:

1. An endocardial electrode arrangement for the intracardiac stimulation of the heart, comprising a conductor assembly including an elongated electric conductor having an electric insulation covering, and a distal end, an electrode head which is electrically conductively connected with the distal end of the conductor, serving the purpose of supplying stimulation pulses to the heart, and conductor assembly emplacement means for the placement of the conductor assembly on the heart wall, characterized in that, for the purpose of placement of the conductor assembly said conductor assembly emplacement means comprises loop means consisting essentially of soft, thin material, mounted on the conductor assembly in proximity to the electrode head, said soft, thin material forming loops on different sides of said conductor assembly each loop including two legs and a free end portion connecting the two legs, and the legs and free end portions of the respective loops projecting from the conductor assembly in respective different directions to facilitate emplacement of the conductor assembly by lifting of the loops from the conductor assembly and adherence of blood within the loops to a heart wall, the loop means being constructed so that the free ends of the loops can be lifted from the conductor assembly by a distance greater than the thickness of said material as measured in a direction radially of the conductor assembly.

2. An endocardial electrode arrangement according to claim 1, characterized in that said conductor assembly emplacement means comprises a plurality of loops (5) arranged along a spiral shaped line about the insulation covering (2) of the elongated electric conductor (1).

3. An endocardial electrode arrangement according to claim 1, characterized in that said conductor assembly emplacement means comprises a plurality of loops (5) arranged along parallel lines in the longitudinal direction of the insulation covering (2) of the elongated electric conductor (1).

4. An endocardial electrode arrangement according to claim 1, characterized in that the loop means (5) is mounted directly on the electric insulation covering (2) of the electric conductor (1).

5. An endocardial electrode arrangement according to claim 1, characterized in that the conductor assembly emplacement means comprises annular mounting means (6) carrying said loop means (5) and slipped over the conductor assembly.

6. An endocardial electrode arrangement according to claim 1, characterized in that the loop means (5) consist of a body-fluid-resistive material.

7. An endocardial electrode arrangement according to claim 1, characterized in that the loop means (5) consist of a reabsorbable material.

8. An endocardial electrode arrangement according to claim 1, characterized in that the loop means (5) in an outwardly extending state, project between one and five millimeters from the surface of the conductor assembly.

9. An endocardial electrode arrangement for the intracardiac stimulation of the heart, comprising a conductor assembly including an elongated electric conductor having an electric insulation covering, and a distal end, an electrode head which is electrically conductively connected with the distal end of the conductor, serving the purpose of supplying stimulation pulses to the heart, and conductor assembly emplacement means for the placement of the conductor assembly on the heart wall, characterized in that, for the purpose of placement of the conductor assembly said conductor assembly emplacement means comprises loop means (5) consisting essentially of soft, thin material, mounted on the conductor assembly (2 or 3) in proximity to the electrode head (3), said conductor assembly together with said electrode head and said emplacement means defining a generally cylindrical electrode configuration in proximity to the electrode head (3) with an outside diameter enabling passage through a vein, said loop means having a loop configuration with a base portion secured with said cylindrical configuration in proximity to said electrode head (3), the loop configuration having two elongated strip portions of the soft thin material extending from the base portion in spaced relationship and in a direction away from said electrode head (3), and having an arcuate connecting strip portion of the soft thin material spaced radially from the cylindrical electrode configuration by a substantial distance and connecting the two elongated strip portions remote from the base portion so as to form a loop with an opening therethrough for accommodating growth of connective tissue into the loop, the loop extending from the base portion at an acute angle to the cylindrical electrode configuration so as to exhibit a divergent relationship to the cylindrical electrode configuration, while being deflectable into close relation to the cylindrical electrode configuration during passage through a vein, and the loop having sufficient resilience so that the loop returns to its divergent relationship to the cylindrical electrode configuration when the loop is moved out of a vein.

10. An endocardial electrode arrangement according to claim 9 with the loop having a divergent relationship to said cylindrical electrode configuration such that the arcuate connecting strip portion is spaced between one and five millimeters from the cylindrical electrode configuration.

11. An endocardial electrode arrangement according to claim 9 with the loop consisting of soft thin synthetic plastic material.

12. An endocardial electrode arrangement according to claim 9 with the loop consisting of soft thin resilient material and being formed from a thin sheet of polyester.

13. An endocardial electrode arrangement according to claim 9, with the loop consisting of soft thin resilient material and being formed from a thin sheet of polypropylene.

14. An endocardial electrode arrangement according to claim 9 with the loop means comprising about eight of said loops spaced about the circumference of said clyindrical electrode configuration.

* * * * *